US011079363B2

(12) United States Patent
Dinsmore

(10) Patent No.: US 11,079,363 B2
(45) Date of Patent: Aug. 3, 2021

(54) SYSTEMS AND METHODS FOR EVALUATING TOXIC GAS SENSORS USING ELECTROCHEMICAL IMPEDANCE SPECTROSCOPY

(71) Applicant: Industrial Scientific Corporation, Pittsburgh, PA (US)

(72) Inventor: Jonathan Eric Dinsmore, Aliquippa, PA (US)

(73) Assignee: Industrial Scientific Corporation, Pittsburgh, PA (US)

( * ) Notice: Subject to any disclaimer, the term of this patent is extended or adjusted under 35 U.S.C. 154(b) by 744 days.

(21) Appl. No.: 15/791,557

(22) Filed: Oct. 24, 2017

(65) Prior Publication Data

US 2019/0041371 A1 Feb. 7, 2019

Related U.S. Application Data

(60) Provisional application No. 62/540,733, filed on Aug. 3, 2017.

(51) Int. Cl.
*G01N 33/00* (2006.01)
*G01N 27/404* (2006.01)
(Continued)

(52) U.S. Cl.
CPC ....... *G01N 33/0006* (2013.01); *G01N 27/026* (2013.01); *G01N 27/404* (2013.01); *G01N 27/4163* (2013.01); *G01N 33/007* (2013.01)

(58) Field of Classification Search
CPC ............. G01N 27/404; G01N 27/4045; G01N 27/4163; G01N 33/0004; G01N 33/0006; G01N 33/007
See application file for complete search history.

(56) References Cited

U.S. PATENT DOCUMENTS 5,298,146 A * 3/1994 Braden ............... G01N 33/0031
204/406
5,932,079 A * 8/1999 Haupt ................ G01N 27/4045
204/412

(Continued)

FOREIGN PATENT DOCUMENTS

CN 110573869 A 12/2019
EP 3662275 A1 6/2020
(Continued)

OTHER PUBLICATIONS

PCT/US18/43093, "International Application Serial No. PCT/US18/43093, International Search Report and Written Opinion dated Oct. 15, 2018", Industrial Scientific Corporation, 12 pages.
(Continued)

*Primary Examiner* — Erika J Villaluna
(74) *Attorney, Agent, or Firm* — GTC Law Group PC & Affiliates

(57) ABSTRACT

The systems and methods of this disclosure enable evaluation, verification, and testing of toxic gas sensors without the need for a target gas cylinder. The systems and methods for testing toxic gas sensors over a broad range of frequencies facilitates evaluation and diagnosis of mechanisms underlying sensor performance. The systems and methods of this disclosure may be incorporated into portable gas sensing equipment for in field diagnostics.

28 Claims, 13 Drawing Sheets

(51) Int. Cl.
      *G01N 27/416*    (2006.01)
      *G01N 27/02*     (2006.01)

(56) References Cited

U.S. PATENT DOCUMENTS

| | | |
|---|---|---|
| 6,428,684 B1 | 8/2002 | Warburton et al. |
| 7,413,645 B2 | 8/2008 | Scheffler et al. |
| 7,959,777 B2 | 6/2011 | Scheffler et al. |
| 8,114,268 B2 * | 2/2012 | Wang ................ A61B 5/14532 204/403.1 |
| 9,046,463 B1 * | 6/2015 | Adler ..................... G01N 27/02 |
| 2008/0214910 A1 | 9/2008 | Buck |
| 2008/0289959 A1 | 11/2008 | West et al. |
| 2011/0199094 A1 * | 8/2011 | Lou .................. G01N 33/0006 324/548 |
| 2013/0060105 A1 * | 3/2013 | Shah ...................... A61B 5/742 600/316 |
| 2015/0101937 A1 | 4/2015 | Woo et al. |
| 2017/0067848 A1 | 3/2017 | Chandrasekhar et al. |
| 2017/0181672 A1 | 6/2017 | Nogueira et al. |

FOREIGN PATENT DOCUMENTS

| | | | | |
|---|---|---|---|---|
| JP | 2012011208 A | * | 1/2012 | ............ C12Q 1/001 |
| WO | 9918430 A1 | | 4/1999 | |
| WO | 0014523 A2 | | 3/2000 | |
| WO | 2019027701 A1 | | 2/2019 | |

OTHER PUBLICATIONS

PCT/US18/43093, "International Application Serial No. PCT/US18/43093, International Preliminary Report on Patentability dated Feb. 13, 2020", Industrial Scientific Corporation, 11 pages.

\* cited by examiner

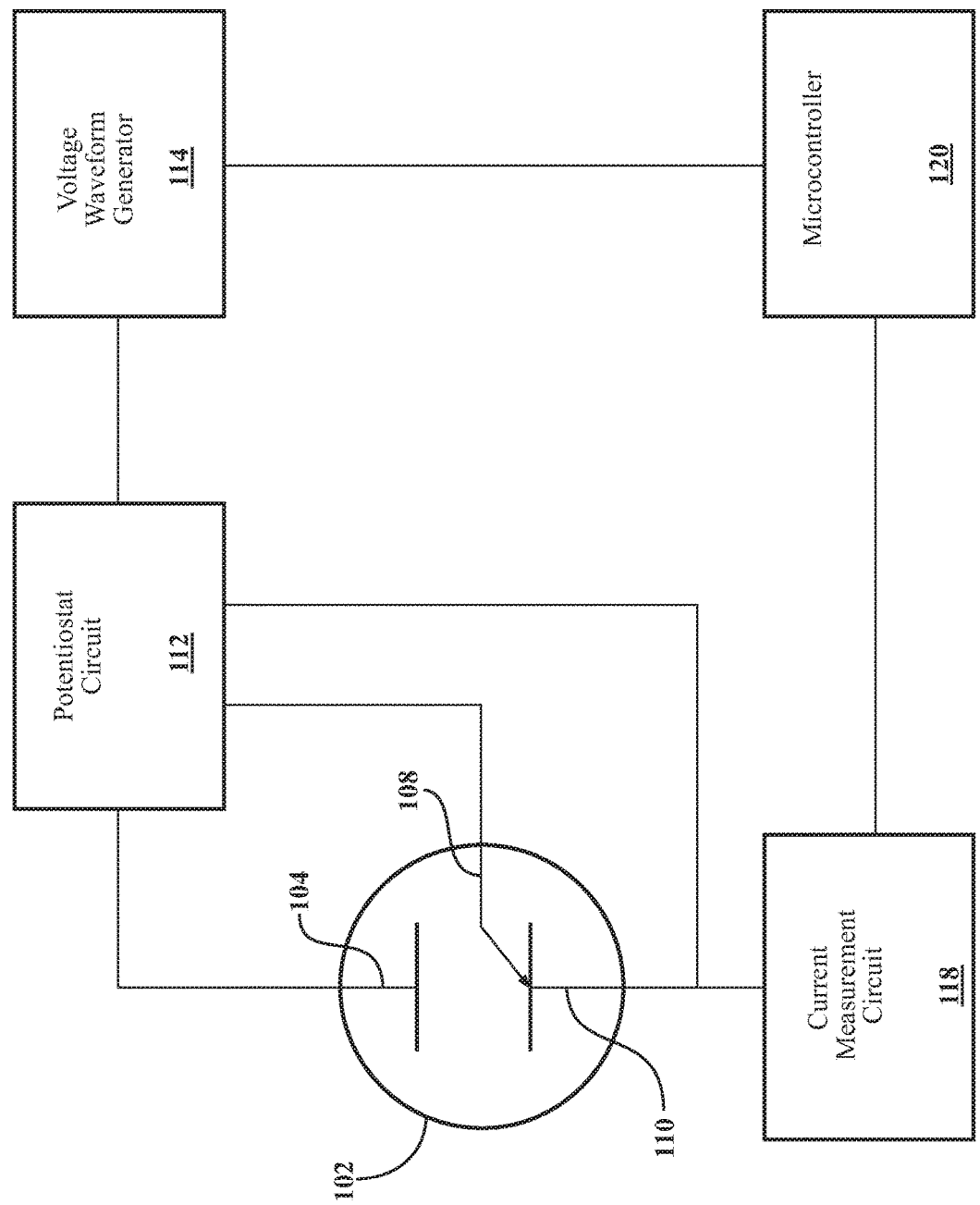

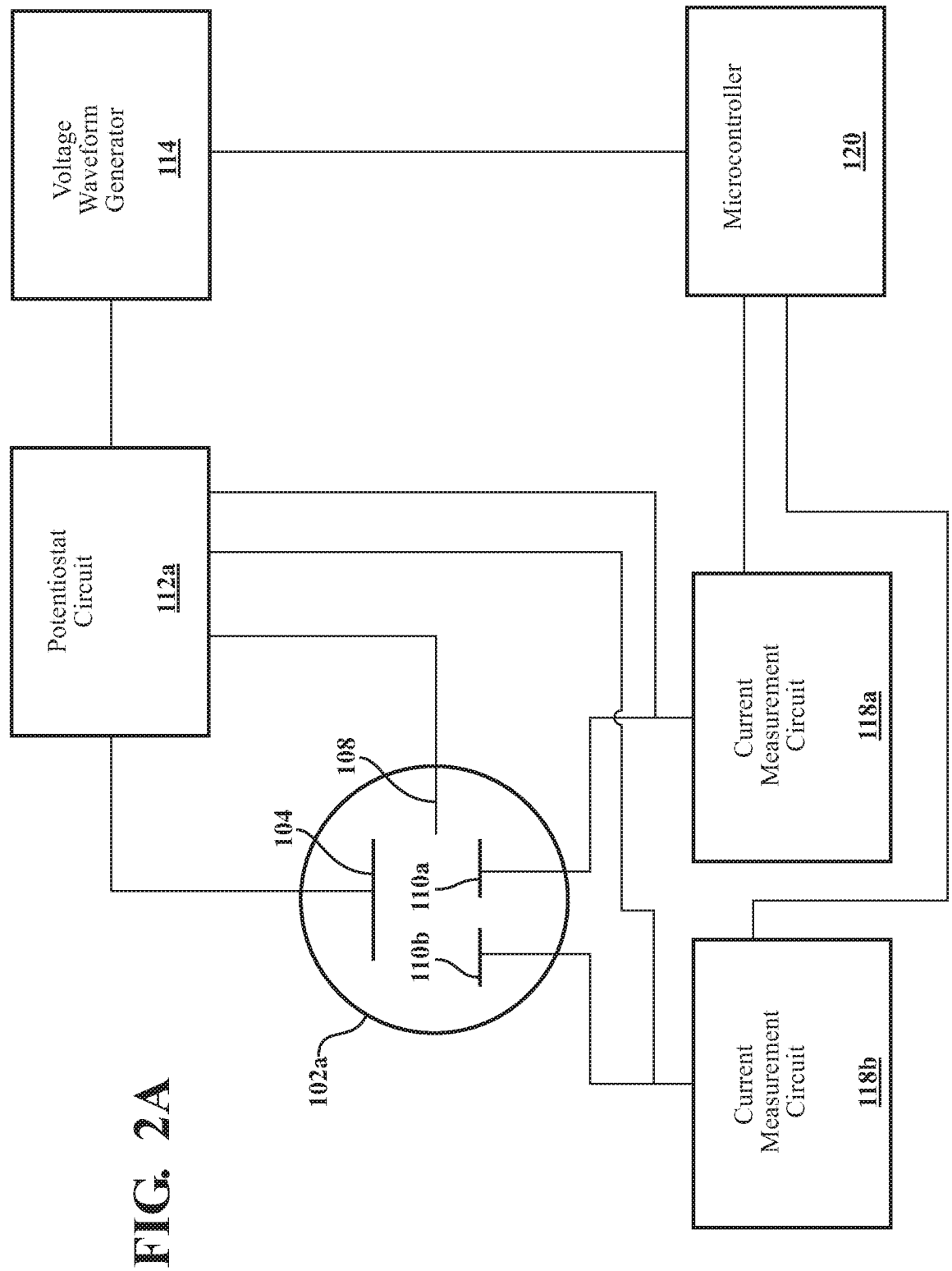

SYSTEMS AND METHODS FOR EVALUATING TOXIC GAS SENSORS USING ELECTROCHEMICAL IMPEDANCE SPECTROSCOPY

CLAIM TO PRIORITY

This application claims priority to U.S. Provisional Appl. No. 62/540,733 (ISCI-0041-P01), filed Aug. 3, 2017, entitled "SYSTEMS AND METHODS FOR EVALUATING TOXIC GAS SENSORS USING ELECTROCHEMICAL IMPEDANCE SPECTROSCOPY."

The above-mentioned patent application is hereby incorporated by reference herein in its entirety.

BACKGROUND

Field

The disclosure relates to the art of toxic gas sensors and particularly to efficient calibration and verification of a toxic gas sensor.

Description of the Related Art

Toxic gas sensors have been widely used in industry to detect and monitor the presence of toxic gases or vapors for safety and environmental purposes. They can provide an early warning of potentially toxic conditions to protect life and property before onset of a hazardous situation.

Various gas sensing technologies are used in different types of gas sensors, such as thermal conductivity sensors, infrared (IR) sensors, electrochemical, semiconductor (MOS) sensors and catalytic bead (or pellistor) sensors.

It is necessary to ensure that electrochemical gas sensors are working correctly in a gas monitoring instrument. Currently, the procedure for doing this requires an application of the target gas to the sensor. The output of the sensor is then monitored and the functionality of the sensor is assessed. Application of the target gas requires a specific gas delivery system, usually consisting of a high pressure cylinder of the target gas, some amount of tubing, flow and pressure regulators, and a manifold to interface with the instrument.

Alternately, there are some techniques to electrically test sensors rather than applying the target gas to the sensor, such as described in U.S. Pat. No. 6,428,684 B1, U.S. Pat. No. 7,959,777 B2, and U.S. Pat. No. 7,413,645 B2. However, these approaches focus on testing only one aspect of the sensor and do not allow the sensor to be completely characterized. Further, there are numerous ways a sensor could fail that would not be detected by these current testing techniques.

Existing testing systems have sought to diagnose sensor performance by means of applying single, very low frequency, pulses to a sensor's counter electrode and observing the response of the working electrode as it recovers from the pulse. By carefully measuring the response from the pulse, the sensor's apparent resistance and capacitance may be determined. Based on the apparent resistance and capacitance, the sensitivity of the sensor may be determined.

However, these measurements of resistance and capacitance are done at very low frequencies and do not accurately characterize the sensor's performance. Electrochemical sensors are not truly capacitors and resistors, so modeling them as such may introduce some degree of error. In the case of single pulse measurements, these errors are such that aspects of the sensor chemistry may not be represented. Measuring the response of the sensor to a single or very low frequency perturbation may not provide sufficient data to distinguish between the apparent capacitance due to diffusion in the electrolyte and the double layer capacitance at the surface of the electrode/electrolyte interface. Similarly, the electrolyte resistance cannot be distinguished from the electrode polarization resistance.

For example, in a carbon monoxide (CO) electrochemical sensor, the sensitivity may change with temperature and with humidity. Both of these effects may result in a shift in apparent capacitance and resistance when tested with a single, or very low frequency pulse. However, the change in temperature may result in a change only in electrolyte resistance, while a change in humidity primarily may result in a change in polarization resistance; except in cases of extreme low humidity which will affect both polarization and electrolyte resistance. Both a drop in humidity and a drop in temperature would result in the sensor losing sensitivity and increasing in response time. Both of these are undesirable. However, prolonged exposure to humidity can cause long term damage to a sensor that could mean it needs to be replaced. Further, a drop in temperature simply needs to be compensated for and does not pose a particular problem for sensor functionality. Because temperature and humidity changes can result in identical shifts in apparent resistance and capacitance at low frequencies, previous techniques would be unable to distinguish between these two phenomena. As a result, proper corrective action cannot be taken.

The current systems evaluate the dynamic behavior of sensors at low frequencies or in response to a single pulse. This appears adequate because the response time of typical electrochemical sensors to their target gas is a few seconds to a few tens of seconds and therefore the sensors are tested at low frequencies, typically less than 10 Hz. However, additional information may be obtained about a sensor by studying its performance at higher frequencies.

There remains a need for a system to fully test and characterize an electrochemical gas sensor as well as accurately diagnose a particular cause of a sensor failure without the need to apply the target calibration gas to the sensor.

SUMMARY

The systems and methods of this disclosure enable verification and testing of toxic gas sensors without the need for a target gas with accompanying gas delivery equipment such as a cylinder and tubing. The systems and methods for testing toxic gas sensors over a broad range of frequencies facilitates evaluation and diagnosis of mechanisms underlying sensor performance. The systems and methods of this disclosure may be incorporated into portable gas sensing equipment for in field diagnostics.

The present disclosure describes a system for evaluating a toxic gas sensor using electrochemical impedance spectroscopy, the system, according to one disclosed non-limiting embodiment of the present disclosure, can include a voltage waveform generator electrically connected to the potentiostat circuit, the voltage wave form generator enabled to input small amplitude voltage sine waves into a reference electrode of the toxic gas sensor, a current measurement circuit electrically connected to the toxic gas sensor, the current measurement circuit enabled to measure amplitude and phase at a counter electrode of the toxic gas sensor in response to the input and a microcontroller electrically connected to the voltage waveform generator and the current measurement circuit, wherein the microcontroller causes the voltage waveform generator to generate a series of voltage sine waves over a frequency range and causes the current measurement circuit to measure the toxic gas sensor response at each frequency, and wherein the microcontroller analyzes the frequency response of the toxic gas sensor.

The present disclosure describes a system for evaluating a toxic gas sensor using electrochemical impedance spectroscopy, the system, according to one disclosed non-limiting embodiment of the present disclosure, can include a potentiostat circuit electrically connected to the toxic gas sensor, a voltage waveform generator electrically connected to the potentiostat circuit, the voltage wave form generator enabled to input small amplitude voltage sine waves into a reference electrode of the toxic gas sensor, a current measurement circuit electrically connected to the toxic gas sensor, the current measurement circuit enabled to measure amplitude and phase at a counter electrode of the toxic gas sensor in response to the input and a microcontroller electrically connected to the voltage waveform generator and the current measurement circuit, wherein the microcontroller causes the voltage waveform generator to generate a series of voltage sine waves over a frequency range and causes the current measurement circuit to measure the toxic gas sensor response at each frequency and wherein the microcontroller analyzes the frequency response of the toxic gas sensor.

The present disclosure describes a system for evaluating a toxic gas sensor using electrochemical impedance spectroscopy, the system, according to one disclosed non-limiting embodiment of the present disclosure, can include a galvanostat circuit electrically connected to the toxic gas sensor a current waveform generator electrically connected to the galvanostat circuit, the current wave form generator enabled to input small amplitude current sine waves into a reference electrode of the toxic gas sensor, a voltage measurement circuit electrically connected to the toxic gas sensor, the voltage measurement circuit enabled to measure amplitude and phase at a counter electrode of the toxic gas sensor in response to the input and a microcontroller electrically connected to the current waveform generator and the voltage measurement circuit, wherein the microcontroller causes the current waveform generator to generate a series of current sine waves over a frequency range and causes voltage current measurement circuit to measure the toxic gas sensor response at each frequency and wherein the microcontroller analyzes the frequency response of the toxic gas sensor.

The present disclosure describes a self-diagnostic toxic gas sensor system, the system, according to one disclosed non-limiting embodiment of the present disclosure, can include a toxic gas sensor, a potentiostat circuit electrically connected to the toxic gas sensor, a voltage waveform generator electrically connected to the potentiostat circuit, the voltage wave form generator enabled to input small amplitude voltage sine waves into a reference electrode of the toxic gas sensor, a current measurement circuit electrically connected to the toxic gas sensor, the current measurement circuit enabled to measure amplitude and phase at a working electrode of the toxic gas sensor in response to the input and a microcontroller electrically connected to the voltage waveform generator and the current measurement circuit, wherein the microcontroller causes the voltage waveform generator to generate a series of voltage sine waves over a frequency range and causes the current measurement circuit to measure the toxic gas sensor response at each frequency and wherein the microcontroller analyzes the frequency response of the toxic gas sensor to diagnose the status of the toxic gas sensor.

The present disclosure describes a system for evaluating a toxic gas electrochemical sensor, the system according to one disclosed non-limiting embodiment of the present disclosure can include a potentiostat circuit electrically connected to the toxic gas electrochemical sensor, a voltage waveform generator connected to the potentiostat circuit and enabled to apply a voltage sine wave at a plurality of selected frequencies to a reference electrode of the toxic gas electrochemical sensor, a current measurement circuit electrically connected to the toxic gas electrochemical sensor for measuring an amplitude and a phase of a current through the toxic gas electrochemical sensor in response to the applied voltage sine wave and a microcontroller electrically connected to the voltage waveform generator and the measurement circuit, wherein the microcontroller controls the voltage waveform generator, receives a corresponding output from the current measurement circuit indicative of the amplitude and the phase of the current through the toxic gas electrochemical sensor at each of the plurality of selected frequencies, and analyzes the output from the current measurement circuit to determine information about a functionality of the toxic gas electrochemical sensor.

A further embodiment of any of the foregoing embodiments of the present disclosure may include systems wherein an amplitude of the applied voltage sine wave is within a range of 5 mV to 50 mV.

A further embodiment of any of the foregoing embodiments of the present disclosure may include systems wherein an amplitude of the applied voltage sine wave is within a range in which the toxic gas electrochemical sensor responds in a linear manner.

A further embodiment of any of the foregoing embodiments of the present disclosure may include systems wherein the plurality of selected frequencies is within a frequency range of 0.1 Hz to 1 MHz.

A further embodiment of any of the foregoing embodiments of the present disclosure may include systems wherein the plurality of selected frequencies includes at least some sequential frequencies that are spaced in unequal increments from each other.

A further embodiment of any of the foregoing embodiments of the present disclosure may include systems wherein analyzing the output comprises calculating a real impedance and an imaginary impedance corresponding to a current or a voltage measurement at each of the plurality of selected frequencies resulting in calculated real impedances and calculated imaginary impedances.

A further embodiment of any of the foregoing embodiments of the present disclosure may include systems wherein analyzing the output further comprises comparing a Nyquist plot of the calculated real impedances and the calculated imaginary impedances with a corresponding reference Nyquist plot of reference real impedances and reference imaginary impedances.

A further embodiment of any of the foregoing embodiments of the present disclosure may include systems wherein the reference real impedances and the reference imaginary impedances are obtained by measuring a newly calibrated toxic gas sensor over a frequency range.

A further embodiment of any of the foregoing embodiments of the present disclosure may include systems wherein analyzing the output further comprises evaluating differences in a location of features of the Nyquist plot of calculated impedances with a location of features of the reference Nyquist plot of reference impedances.

A further embodiment of any of the foregoing embodiments of the present disclosure may include systems wherein if a functional change in the toxic gas electrochemical sensor is identified by analyzing the output, then the microcontroller performs at least one of: updating a calibration for the toxic gas electrochemical sensor, updating a calibration for a piece of equipment associated with the toxic gas electrochemical sensor, disabling a piece of equipment associated with the toxic gas electrochemical sensor, and alerting a user.

A further embodiment of any of the foregoing embodiments of the present disclosure may include systems wherein the toxic gas electrochemical sensor is one of a carbon monoxide sensor, an ammonia electrochemical sensor, a hydrogen sulfide sensor, and an oxygen sensor.

A further embodiment of any of the foregoing embodiments of the present disclosure may include systems wherein the toxic gas electrochemical sensor is a three electrode sensor having the reference electrode, a working electrode, and a counter electrode.

A further embodiment of any of the foregoing embodiments of the present disclosure may include systems wherein the current measurement circuit is connected to the working electrode or the counter electrode.

A further embodiment of any of the foregoing embodiments of the present disclosure may include systems wherein the toxic gas electrochemical sensor includes either two or four electrode terminals.

A further embodiment of any of the foregoing embodiments of the present disclosure may include systems wherein the toxic gas electrochemical sensor is a two electrode terminal sensor including a working electrode and the reference electrode, wherein the reference electrode is a combination counter/reference electrode.

A further embodiment of any of the foregoing embodiments of the present disclosure may include systems wherein the toxic gas electrochemical sensor is a four electrode sensor able to detect at least two different detectable gases, wherein the four electrode sensor comprises the reference electrode, a counter electrode, and at least two working electrodes, wherein each of the at least two working electrodes corresponds to a respective one of the at least two different detectable gases.

A further embodiment of any of the foregoing embodiments of the present disclosure may include systems wherein the current measurement circuit comprises at least two current measurement circuits, wherein each of the at least two current measurement circuits measures current at a respective one of the at least two working electrodes.

A further embodiment of any of the foregoing embodiments of the present disclosure may include systems wherein information about a functionality of the toxic gas electrochemical sensor comprises information regarding a change in the bulk electrolyte resistance of the toxic gas electrochemical sensor, a change in the freedom of diffusion of ions within the toxic gas electrochemical sensor or a change in the effective polarization impedance of the electrode/electrolyte interface.

A further embodiment of any of the foregoing embodiments of the present disclosure may include systems wherein information about a functionality of the toxic gas electrochemical sensor comprises information regarding a change in the sensitivity of the toxic gas electrochemical sensor or a change in the response time of the toxic gas electrochemical sensor.

The present disclosure describes a method for evaluating a toxic gas electrochemical sensor using electrochemical impedance spectroscopy, the system according to one disclosed non-limiting embodiment of the present disclosure can include applying a current or a voltage sine wave at a plurality of selected frequencies to a reference electrode of the toxic gas sensor, measuring a voltage or a current response of the toxic gas sensor corresponding to each of the plurality of selected frequencies and analyzing the measured voltage response or the measured current response over the plurality of selected frequencies to determine information about a function of the toxic gas sensor.

A further embodiment of any of the foregoing embodiments of the present disclosure may include methods wherein analyzing the measured voltage response or the measured current response comprises calculating a real impedance and an imaginary impedance for each of the plurality of selected frequencies resulting in a calculated real impedance and a calculated imaginary impedance.

A further embodiment of any of the foregoing embodiments of the present disclosure may include methods wherein analyzing the measured voltage response or the measured current response further comprises comparing, for a plurality of key frequencies, the calculated real impedance and the calculated imaginary impedance against a reference real impedance and a reference imaginary impedance.

The present disclosure describes a system for evaluating a toxic gas electrochemical sensor, the system according to one disclosed non-limiting embodiment of the present disclosure can include a galvanostat circuit electrically connected to the toxic gas electrochemical sensor, a current waveform generator connected to the galvanostat circuit and enabled to apply a current sine wave at a plurality of selected frequencies to a reference electrode of the toxic gas electrochemical sensor, a voltage measurement circuit electrically connected to the toxic gas electrochemical sensor for measuring an amplitude and a phase of a voltage across the toxic gas electrochemical sensor in response to the applied current sine wave and a microcontroller electrically connected to the current waveform generator and the measurement circuit, wherein the microcontroller controls the current waveform generator, receives a corresponding output from the voltage measurement circuit indicative of the amplitude and phase of the voltage across the toxic gas electrochemical sensor at each of the plurality of selected frequencies, and analyzes the output to determine information about a functionality of the toxic gas electrochemical sensor.

A further embodiment of any of the foregoing embodiments of the present disclosure may include systems wherein an amplitude of the applied current sine wave is within a range of 1 nA to 1 mA.

A further embodiment of any of the foregoing embodiments of the present disclosure may include systems wherein the plurality of selected frequencies is within a frequency range of 0.1 Hz to 1 MHz.

A further embodiment of any of the foregoing embodiments of the present disclosure may include systems wherein analyzing the output comprises calculating a real impedance and an imaginary impedance corresponding to a current or a voltage measurement at each of the plurality of selected frequencies, and comparing a Nyquist plot of the calculated real impedance and the calculated imaginary impedance with a corresponding reference Nyquist plot of reference real impedances and reference imaginary impedances.

A further embodiment of any of the foregoing embodiments of the present disclosure may include systems wherein information about a functionality of the toxic gas electrochemical sensor comprises information regarding a change in the bulk electrolyte resistance of the toxic gas electrochemical sensor or a change in the freedom of diffusion of ions within the toxic gas electrochemical sensor.

A further embodiment of any of the foregoing embodiments of the present disclosure may include systems wherein information about a functionality of the toxic gas electrochemical sensor comprises information regarding a change in the sensitivity of the toxic gas electrochemical sensor or a change in the response time of the toxic gas electrochemical sensor.

These and other systems, methods, objects, features, and advantages of the present disclosure will be apparent to those skilled in the art from the following detailed description of the preferred embodiment and the drawings.

All documents mentioned herein are hereby incorporated in their entirety by reference. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context.

BRIEF DESCRIPTION OF THE FIGURES

The disclosure and the following detailed description of certain embodiments thereof may be understood by reference to the following figures:

FIG. 1A depicts a test system embodiment for an exemplary three electrode gas sensor.

FIG. 2A depicts a test system embodiment for an exemplary four electrode gas sensor.

DETAILED DESCRIPTION

Figure 1B:
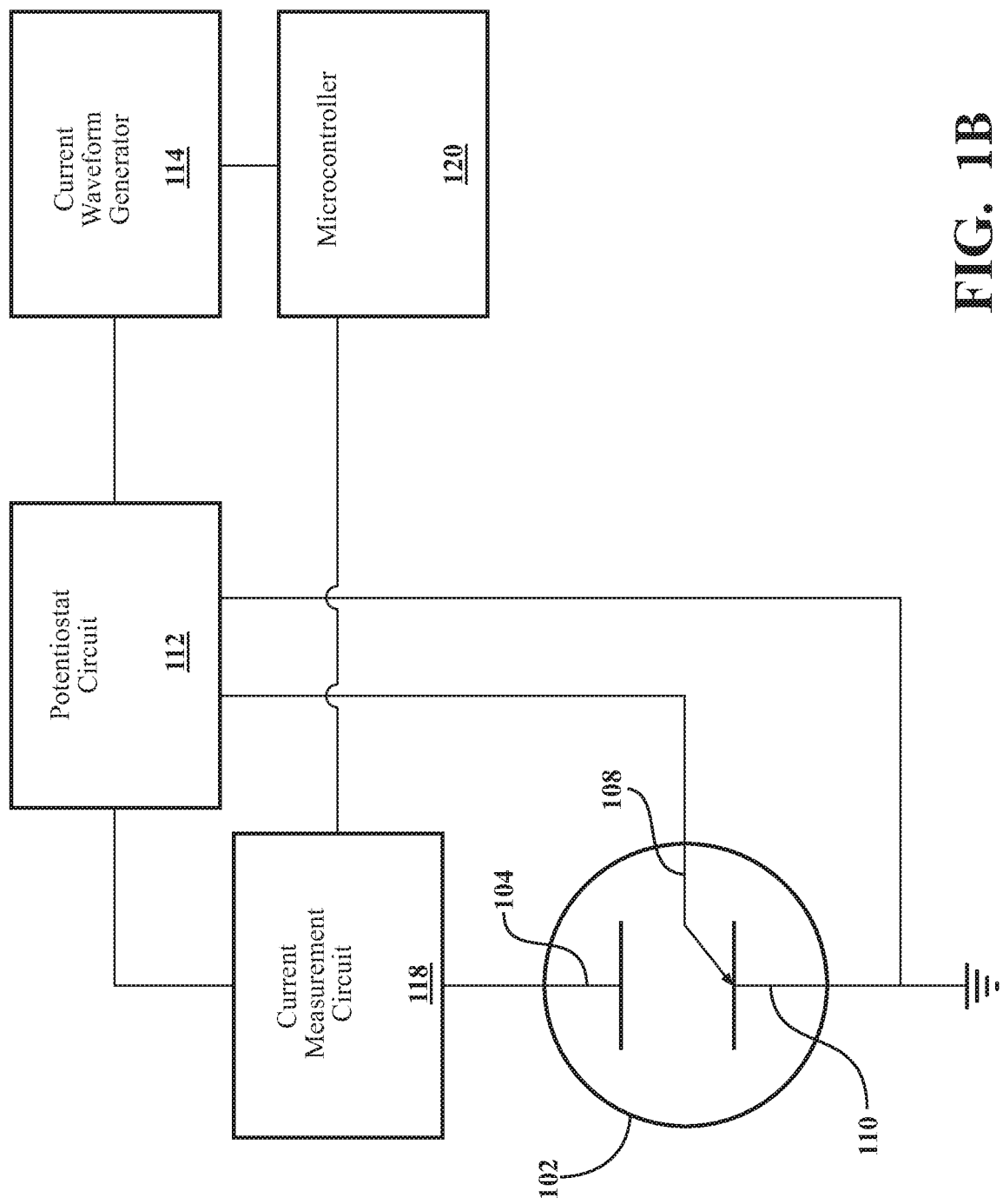
FIG. 1B depicts another test system embodiment for an exemplary three electrode gas sensor.

The described system enables the functionality of a sensor to be determined without the need to apply a high pressure cylinder of the target gas to the sensor. The system operates by applying specific electrical stimuli to the sensor and measuring the sensor response. This enables sensor functionality checks to be performed without the need for trained personnel to apply a target gas and ensure that the gas delivery equipment is functioning correctly. Thus, any faults in the sensor may be detected without the need for traditional gas testing apparatus.

As shown in FIG. 1A, a block diagram of an embodiment of the test system includes an electrochemical sensor 102 comprising a counter electrode 104, a reference electrode 108 and a working electrode 110, which may be maintained at a stable operating point by a potentiostat circuit 112, as is known in the art. A voltage waveform generator 114 may feed small amplitude voltage sine waves into the potentiostat circuit 112 and to the electrochemical sensor 102 over a range of frequencies, such as 1 MHz to 0.1 Hz. The current amplitude and phase of the response of the electrochemical sensor 102 to the input sine waves are measured at the working electrode by the current measurement circuit 118. The voltage waveform generator 114 is controlled by a microcontroller 120. The microcontroller 120 takes the measurements from the current measurement circuit 118 and uses them to calculate the impedance of the electrochemical sensor 102 at various selected frequencies in the input frequency range.

The amplitude of the input voltage sine waves may be selected to be as large as possible while still maintaining a linear response by the toxic gas electrochemical sensor 102. While the actual voltage amplitude for testing may be specific to the toxic gas electrochemical sensor under test, in embodiments, the input voltage sine waves may have an amplitude in the range of 5 mV to 50 mV.

FIG. 1B illustrates a block diagram of another embodiment of a test system, wherein an electrochemical sensor 102 comprising a counter electrode 104, a reference electrode 108 and a working electrode 110 may be maintained at a stable operating point by a potentiostat circuit 112, as is known in the art. A voltage waveform generator 114 is connected to a potentiostat circuit 112 such that voltage sine waves of small amplitude may be injected into the reference electrode 108, such as at frequencies ranging from 1 MHz to 0.1 Hz. The current amplitude and phase response of the electrochemical sensor 102 are measured at the counter electrode 104 and analyzed by a microcontroller 120.

FIG. 2A illustrates a block diagram of another embodiment of a test system for an electrochemical sensor 102a having four electrodes; a counter electrode 104, a reference electrode 108 and two working electrodes 110a, 110b. Each of the working electrodes 110a, 110b may be comprised of different materials such that each working electrode 110a, 110b is sensitive to a different toxic gas. Each working electrode 110a, 110b would produce a current proportional to its respective target gas. One example of a four electrode sensor is the "COSH" sensor which is sensitive to both CO (carbon monoxide) and H2S (hydrogen sulfide). The electrochemical sensor 102a may be maintained at a stable operating point by a potentiostat circuit 112a, as is known in the art. A voltage waveform generator 114 is connected to a potentiostat circuit 112a such that voltage sine waves of small amplitude may be injected into the reference electrode 108, such as at frequencies ranging from 1 MHz to 0.1 Hz. The current amplitude and phase of the response of the electrochemical sensor 102a to the input sine waves are measured at each working electrode 110a, 110b by a current measurement circuit 118a, 118b. The voltage waveform generator 114 is controlled by a microcontroller 120. The microcontroller 120 takes the measurements from the current measurement circuits 118a, 118b for each of the working electrodes 110a, 110b and uses them to calculate the impedance of the electrochemical sensor 102a at various frequencies in the input frequency range for the different working electrodes 110a, 110b.

Figure 2B:
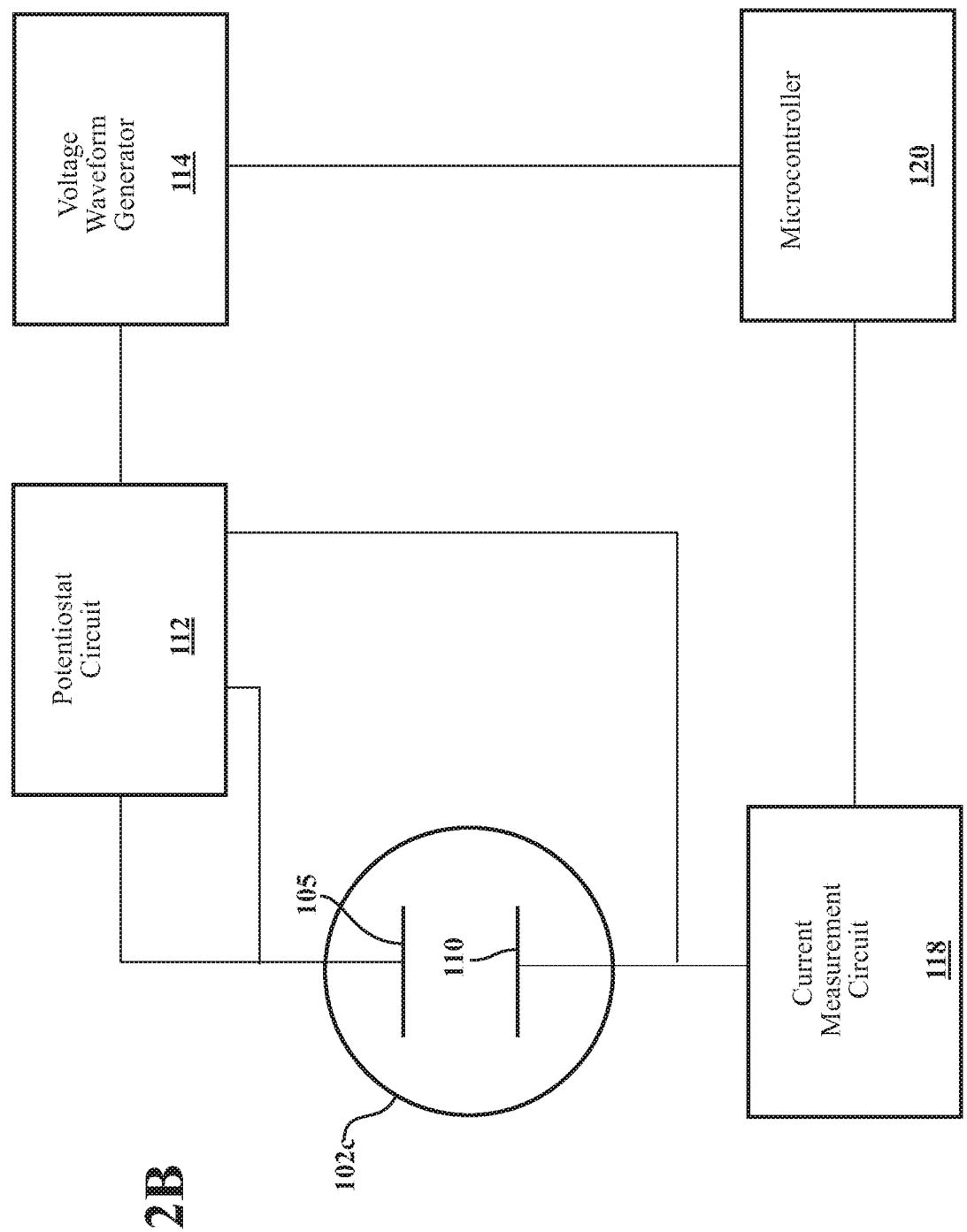
FIG. 2B depicts a test system embodiment for an exemplary two electrode gas sensor.

FIG. 2B illustrates a block diagram of another embodiment of a test system for a two electrode electrochemical sensor 102c with a combination counter/reference electrode 105 and a working electrode 110c which may be maintained at a stable operating point by a potentiostat circuit 112, as is known in the art. A voltage waveform generator 114 may feed small amplitude voltage sine waves into the potentiostat circuit 112 over a range of frequencies, such as 1 MHz to 0.1 Hz. The current amplitude and phase of the response of the electrochemical sensor 102c to the input sine waves are measured at the working electrode 110c by the current measurement circuit 118. The voltage waveform generator 114 is controlled by a microcontroller 120. The microcontroller 120 takes the measurements from the current measurement circuit 118 and uses them to calculate the impedance of the electrochemical sensor 102c at various frequencies in the input frequency range.

Figure 2C:
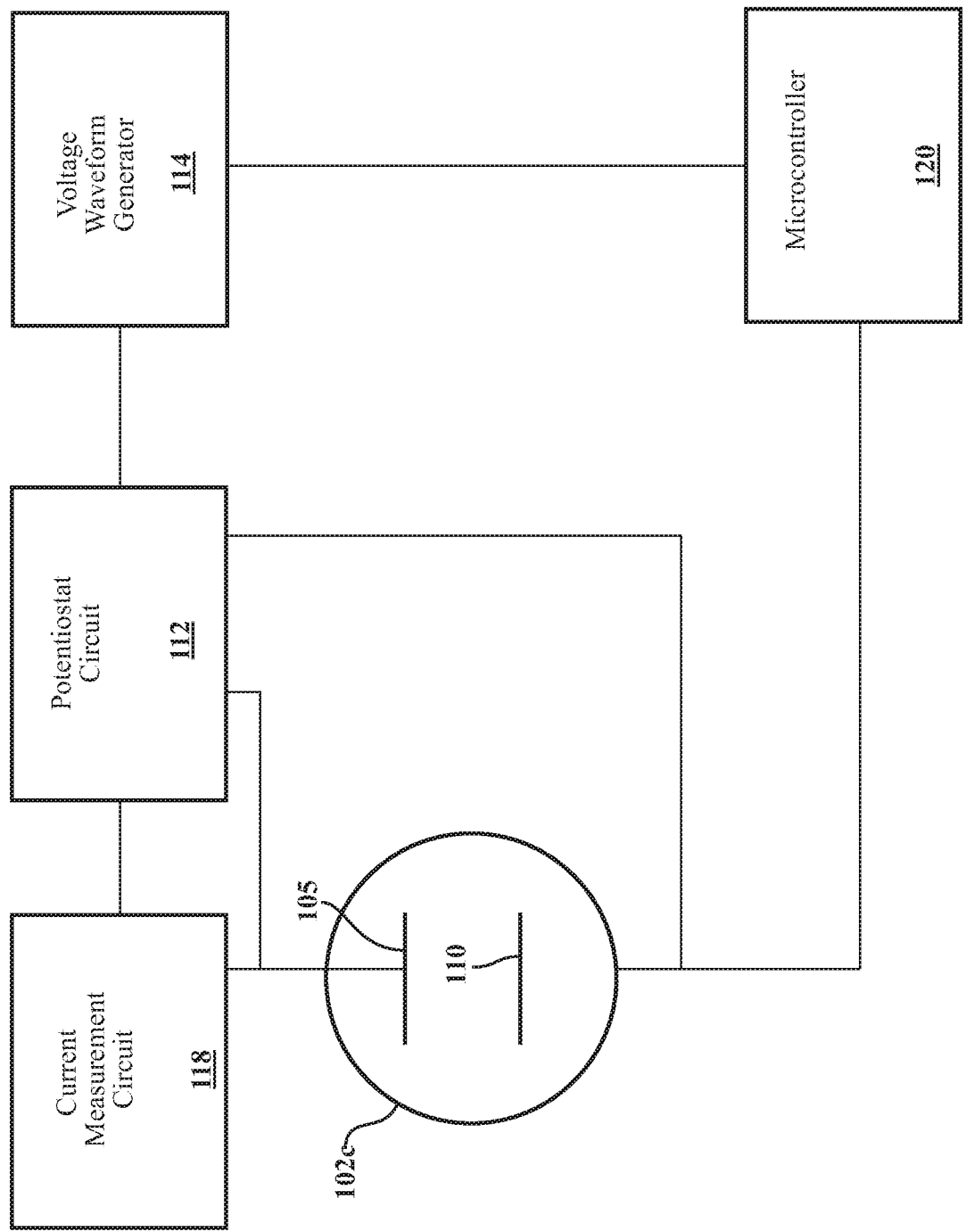
FIG. 2C depicts another test system embodiment for an exemplary two electrode gas sensor.

FIG. 2C illustrates a block diagram of another embodiment of a test system for a two electrode electrochemical sensor 102c with a combination counter/reference electrode 105 and a working electrode 110c which may be maintained at a stable operating point by a potentiostat circuit 112, as is known in the art. A voltage waveform generator 114 may feed small amplitude voltage sine waves into the potentiostat circuit 112 over a range of frequencies, such as 1 MHz to 0.1 Hz. The current amplitude and phase of the response of the electrochemical sensor 102c to the input sine waves are measured at the combination counter/reference electrode 105 by the current measurement circuit 118. The voltage waveform generator 114 is controlled by a microcontroller 120. The microcontroller 120 takes the measurements from the current measurement circuit 118 and uses them to calculate the impedance of the electrochemical sensor 102c at various frequencies in the input frequency range.

Figure 3:
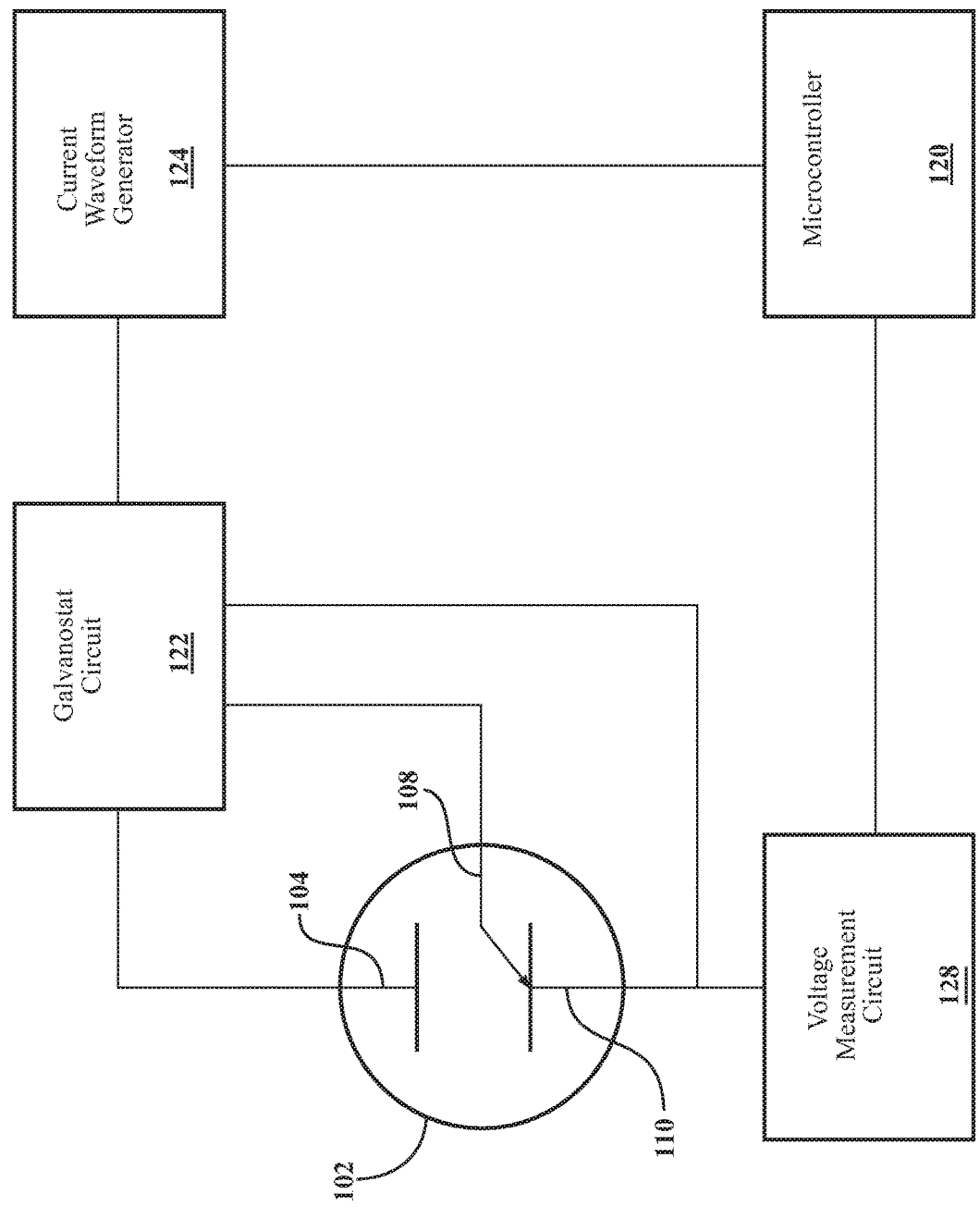
FIG. 3 depicts a test system embodiment for an exemplary three electrode gas sensor and which includes a galvanostat circuit.

As shown in the block diagram of FIG. 3, an electrochemical sensor 102 with counter electrode 104, reference electrode 108 and working electrode 110 is maintained at a stable operating point by the galvanostat circuit 122, as is known in the art. A current waveform generator 124 is connected to the galvanostat circuit 122 such that small amplitude current sine waves may be fed into the electrochemical sensor 102 at frequencies ranging from 1 MHz to 0.1 Hz. The voltage amplitude and phase response of the electrochemical sensor 102 is measured at the counter electrode 104 by the voltage measurement circuit 128. The current waveform generator 124 is controlled by the microcontroller 120. The microcontroller 120 takes the amplitude and phase response measurements from the voltage measurement circuit 128 and uses them to calculate the impedance of the electrochemical sensor 102 at various frequencies.

In the illustrated embodiments, the signal applied to the electrochemical sensor 102 by a signal generator (a current waveform generator or a voltage waveform generator) is small enough in amplitude that the electrochemical sensor 102 responds in a linear manner. This allows the electrochemical sensor 102 to quickly recover from the test and resume normal operation. Also, if the electrochemical sensor 102 response becomes non-linear the response may introduce other frequency harmonics into the sensor response making analysis of the electrochemical sensor 102 output much less accurate.

In embodiments, the microcontroller 120 analyzes the amplitude and phase response of the electrochemical sensor 102 and calculates the real and imaginary impedance of the electrochemical sensor 102 for each of a plurality of selected frequencies in the frequency range of the voltage or current injected into the electrochemical sensor 102 by the waveform generator. Based on the analysis of the amplitude and phase response of the electrochemical sensor 102, the microcontroller 120 may apply algorithms that enable it to determine various parameters representative of the electrochemical sensor's 102 internal chemistry. These parameters may be used to assess the electrochemical sensor's 102 functionality and predict the electrochemical sensor's 102 performance.

The described systems may be incorporated in personal protective equipment or tools. If an electrochemical sensor's performance is predicted to deviate from a reference performance for the type of toxic gas sensor, the microcontroller may perform one or more of: provide calibration files for the toxic gas sensor; provide calibration files for a personal protective equipment associated with the toxic gas sensor or a tool associated with the toxic gas sensor; issue an alert to a user of the piece of personal protective equipment or tool; request that the user take some corrective action such as calibrating the sensor; log a discrepancy in performance of the toxic gas sensor; log a potential discrepancy in performance of a tool or piece of protective equipment; shut off a piece of equipment associated with the toxic gas sensor; disable the toxic gas sensor; and the like.

Several experiments demonstrate the correlation between electrochemical impedance spectroscopy (EIS) spectrum response and the electrochemical sensor 102 performance. One of the most significant problems affecting electrochemical sensors 102 is long term exposure to low humidity environments; this is particularly true of CO (carbon monoxide) electrochemical sensors 102. Exposure to low humidity environments for long periods of time may result in a decrease of the CO sensor's sensitivity and an increase in the response time.

In a non-limiting example, a set of CO electrochemical sensors 102 was placed in an environment with humidity of about 40% relative humidity (RH) and allowed to stabilize for 14 days. The sensitivity and response time of the electrochemical sensors 102 were measured using traditional measurement techniques based on the application of the target gas, in this case carbon monoxide. The EIS spectra of the electrochemical sensors 102 were then measured using a system similar to that illustrated in FIG. 1.

The electrochemical sensors 102 were then placed in an environment with humidity of about 10% RH and allowed to stabilize for 2 weeks. The sensitivity and response time of the electrochemical sensors 102 were then measured again using traditional measurement techniques based on the application of the target gas, in this case carbon monoxide. The EIS spectra of the electrochemical sensors 102 were then measured using the system of FIG. 1 for a second time.

Using traditional techniques, including a lab potentiostat to bias and measure the sensors and a gas delivery system that applies a known concentration of gas to the sensors, the response of the sensors was measured by the potentiostat. The results indicated that the average sensitivity of the electrochemical sensor 102 decreased by about 14%, from an average of 0.067 uA/ppm at 40% RH to an average of 0.064 uA/ppm at 10% RH, while the response time tripled going from an average of about 11 seconds at 40% RH to an average of about 32 seconds at 10% RH.

Figure 4:
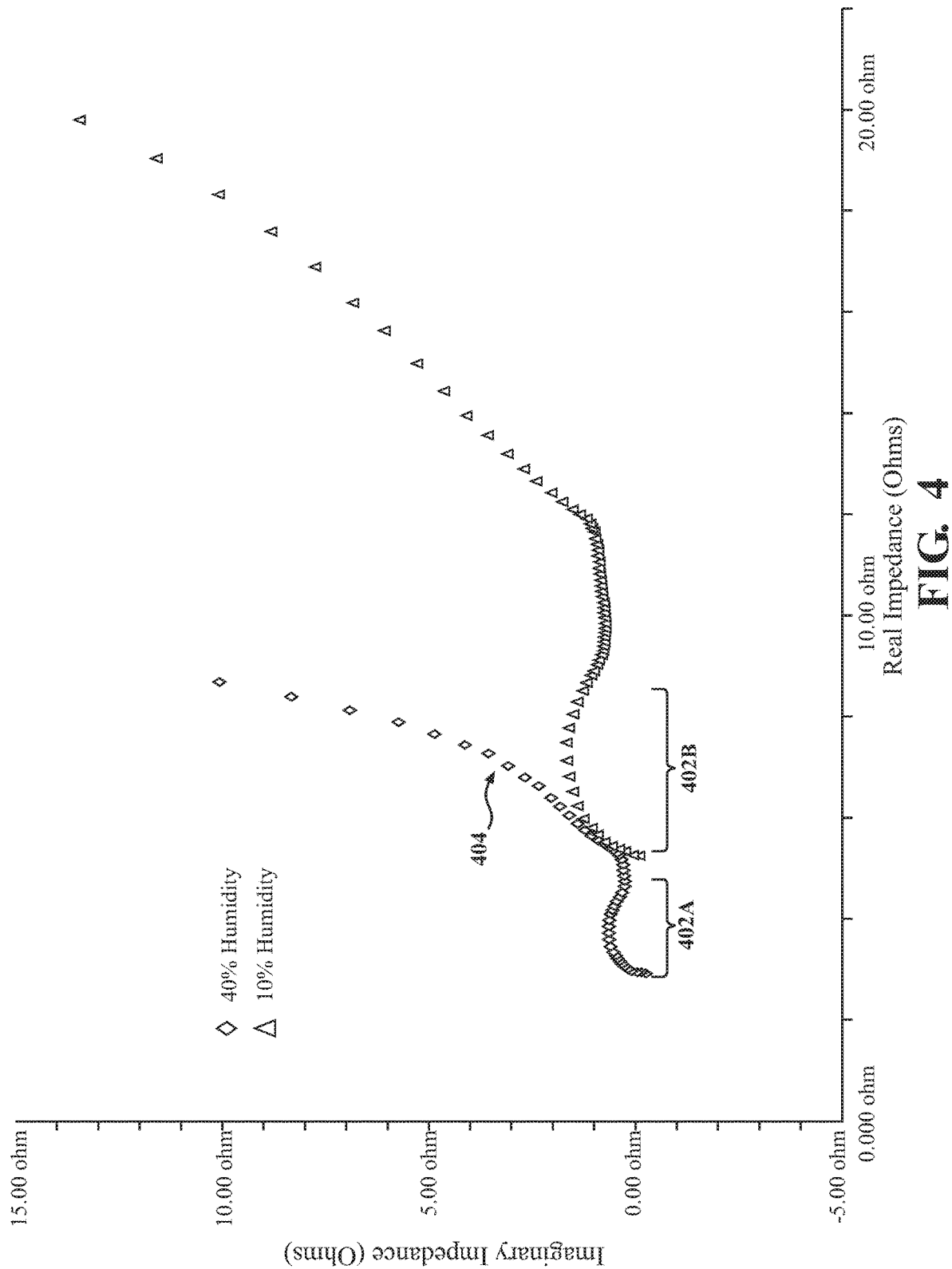
FIG. 4 depicts a Nyquist diagram showing a carbon monoxide sensor response under two different humidity conditions.

These changes in electrochemical sensor performance are mirrored in the EIS spectrum as well. A Nyquist plot (FIG. 4) shows impedance measurements as an input waveform is varied in frequency from 0.1 Hz to 1 MHz for an electrochemical sensor 102 at 10% RH and at 40% RH. The horizontal axis of FIG. 4 shows real impedance while the vertical access shows imaginary impedance. The data on the left shown as diamonds represents measurements that were taken when the electrochemical sensor 102 was at 40% RH while the data on the right, shown as triangles, represent measurements that were taken when the electrochemical sensor 102 was at 10% RH. Analysis of the graphs indicate that the electrochemical sensor's 102 impedance increased as the humidity decreased from 40% RH on the left hand side to 10% RH on the right hand side as may be seen in the overall shift in the measurement curve to higher impedances. Analysis of the relative "diameters" of the half circle portions 402A, 402B of the two plots indicates that effective polarization impedance of the electrode/electrolyte interface increased as the humidity decreased as seen by the increased "diameter" of the half circle portion 402B of the response at 10% RH relative to the "diameter" of the half circle portion 402A of the response at 40% RH. Similarly, the left most point on the plot for each data set shows that the bulk electrolyte resistance also increased as the humidity decreased as the bulk electrolyte resistance at 40% is approximately half the bulk electrolyte resistance at 10%. Also, the rate/freedom of diffusion of ions within the sensor can be seen as the slope of the line on the right side of each plot. In the 40% RH plot, the line starts from the trough at the end of the circle going up at about a 45 degree slope. It then increases its slope at inflection point 404, indicating a change from a free diffusion system to a bounded diffusion system. In the 10% RH plot, there isn't a clear change in slope, appearing to indicate that the boundary between a free diffusion system and a bounded diffusion system is less clearly defined.

Figure 5:
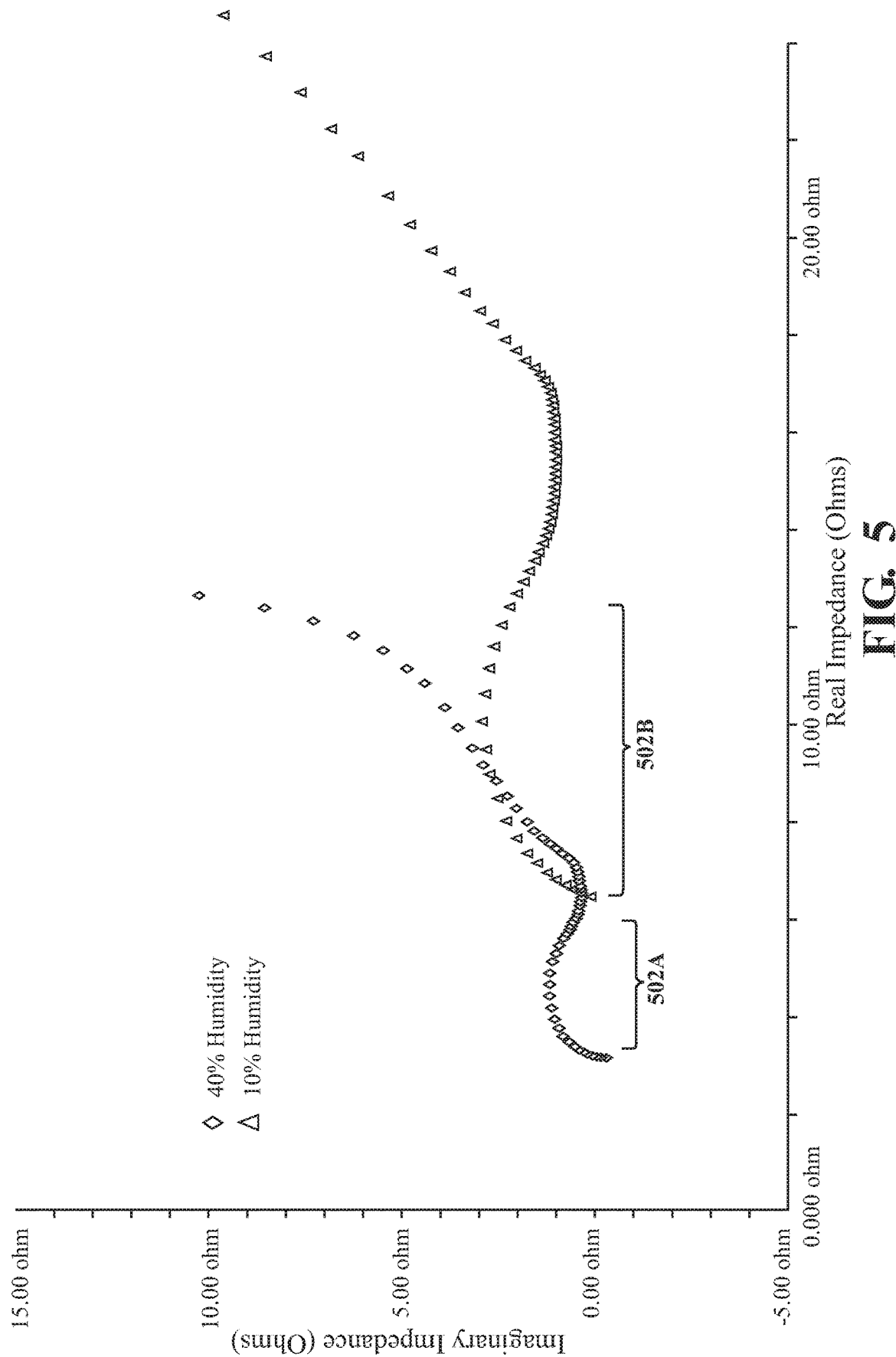
FIG. 5 depicts a Nyquist diagram showing a second carbon monoxide sensor response under two different humidity conditions.

The Nyquist plot of FIG. 5 shows similar features for impedance measurements as an input waveform is varied in frequency from 0.1 Hz to 1 MHz for a different CO electrochemical sensor 102 at 10% RH (triangles) and at 40% RH (diamonds). Again, analysis of the graph indicates that the electrochemical sensor's 102 impedance increased as the humidity decreased from 40% RH on the left hand side to 10% RH on the right hand side as may be seen in the overall shift in the measurement curve to higher impedances. Analysis of the relative "diameters" of the half circle portions 502A, 502B of the two plots indicates that effective polarization impedance of the electrode/electrolyte interface increased as the humidity decreased as seen by the increased "diameter" of the half circle portion 502B of the response at 10% RH relative to the "diameter" of the half circle portion 502A of the response at 40% RH.

Figure 6:
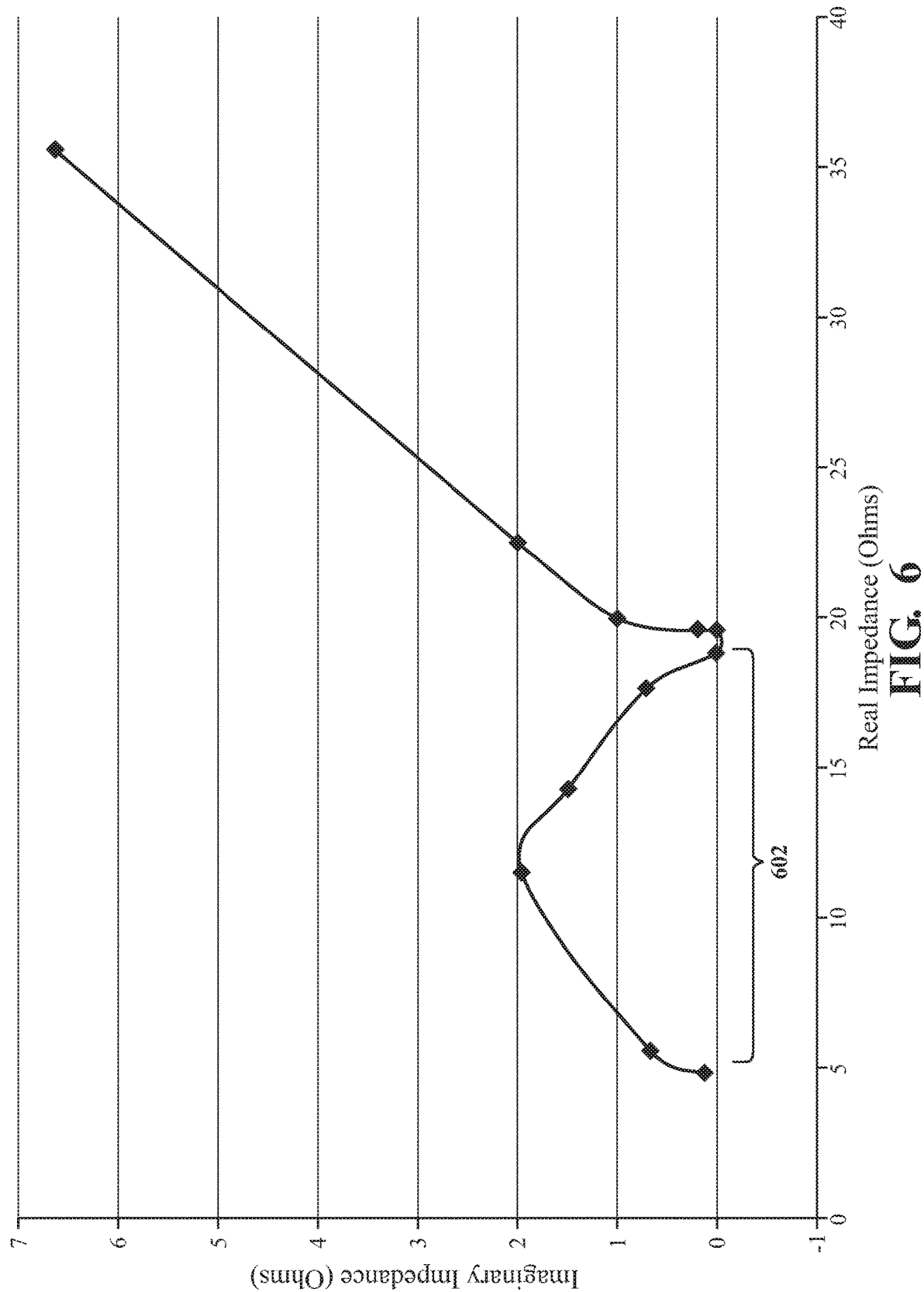
FIG. 6 depicts a Nyquist diagram of a carbon monoxide sensor measured on the system of FIG. 2.

An electrochemical sensor 102 measured in different system embodiments may result in similar response curves. A Nyquist plot (FIG. 6) shows impedance measurements as an input waveform is varied in frequency from 0.1 Hz to 1 MHz for the same electrochemical sensor 102 as measured in FIG. 4 but measured using the system of FIG. 2. The graphs show similar features such as the effective polarization impedance of the electrode/electrolyte interface represented by the "diameter" 602 of the response.

Figure 7:
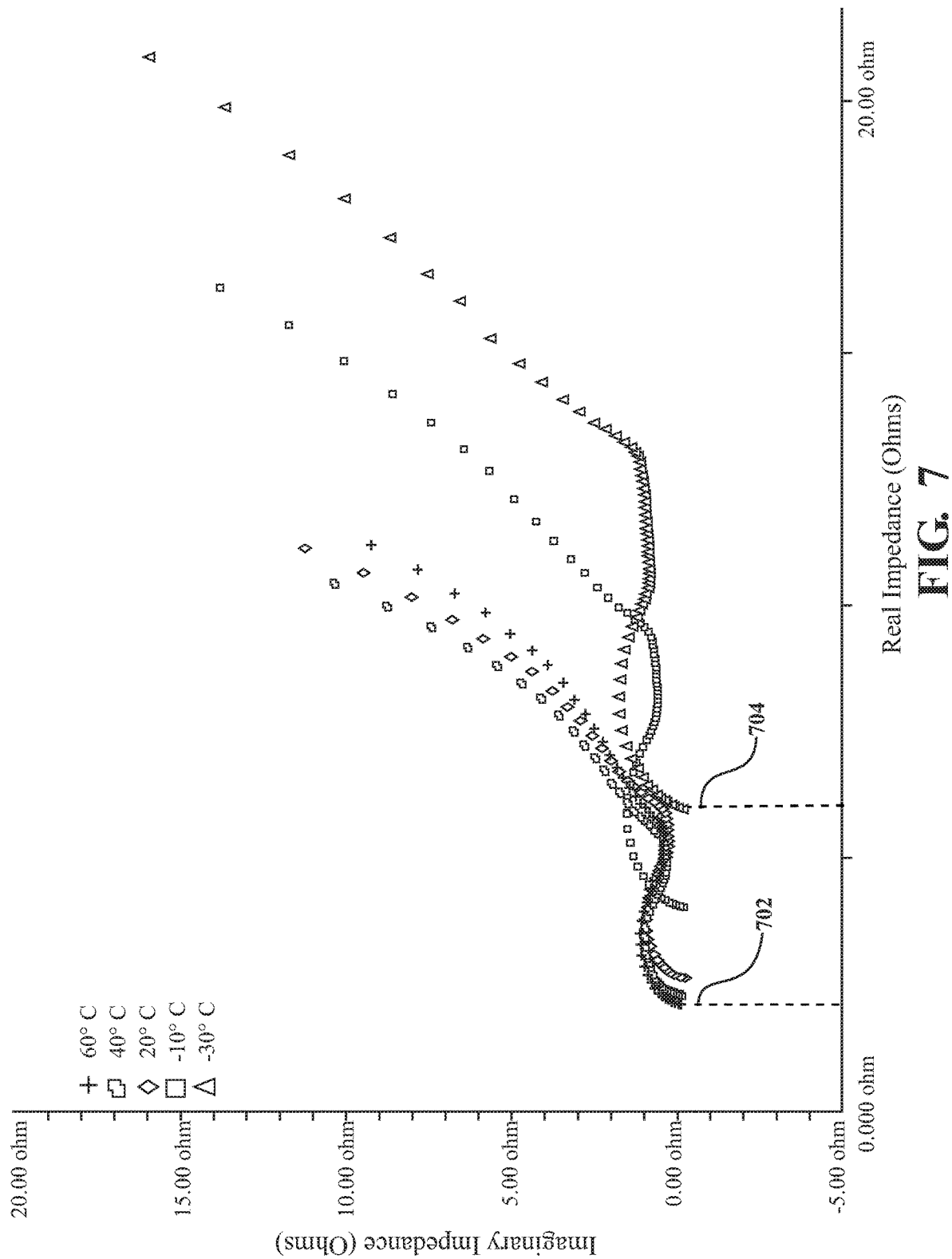
FIG. 7 depicts a Nyquist diagram showing a carbon monoxide sensor response under five different temperature conditions.

A Nyquist plot (FIG. 7) shows changes in impedance measurements as an input waveform is varied in frequency from 0.1 Hz to 1 MHz for a CO electrochemical sensor 102 at temperatures ranging from −30° Celsius to +60° Celsius. The horizontal axis shows real impedance while the vertical access shows imaginary impedance. As illustrated, the sensor demonstrates increased real impedance with decreasing temperature as shown by the increase in the lowest level of real impedance between 702 and 704.

A Nyquist plot of the measured impedances may be compared to a reference Nyquist plot measured on the same sensor when newly calibrated. The measurements for the reference Nyquist plot may be taken when the sensor is new in the factory or on subsequent occasions when the sensor is freshly calibrated. The sensor may be calibrated using a reference gas as described elsewhere prior to obtaining measurements for a reference Nyquist plot. Changes in the position or size of features such as inflection points, diameter, and/or starting impedance of circles or half circles, and the like on the measured Nyquist plot relative to the reference Nyquist plot may be used to analyze the performance of the electrochemical sensor and identify a change in the sensitivity of the toxic gas electrochemical sensor sensitivity or a change in response time relative to the performance at the time of the reference measurements. The measurements of the sensor may be taken more frequently (at smaller frequency intervals) at frequencies surrounding expected features as seen in the reference Nyquist plot.

If the sensor is measured at a different temperature for the measured Nyquist plot compared to the temperature at which the reference Nyquist plot was measured, compensation for the shift in response with temperature, which is fairly consistent from sensor to sensor, may be applied. This may enable improved analysis of response differences related to humidity or sensor poisoning.

Figure 8:
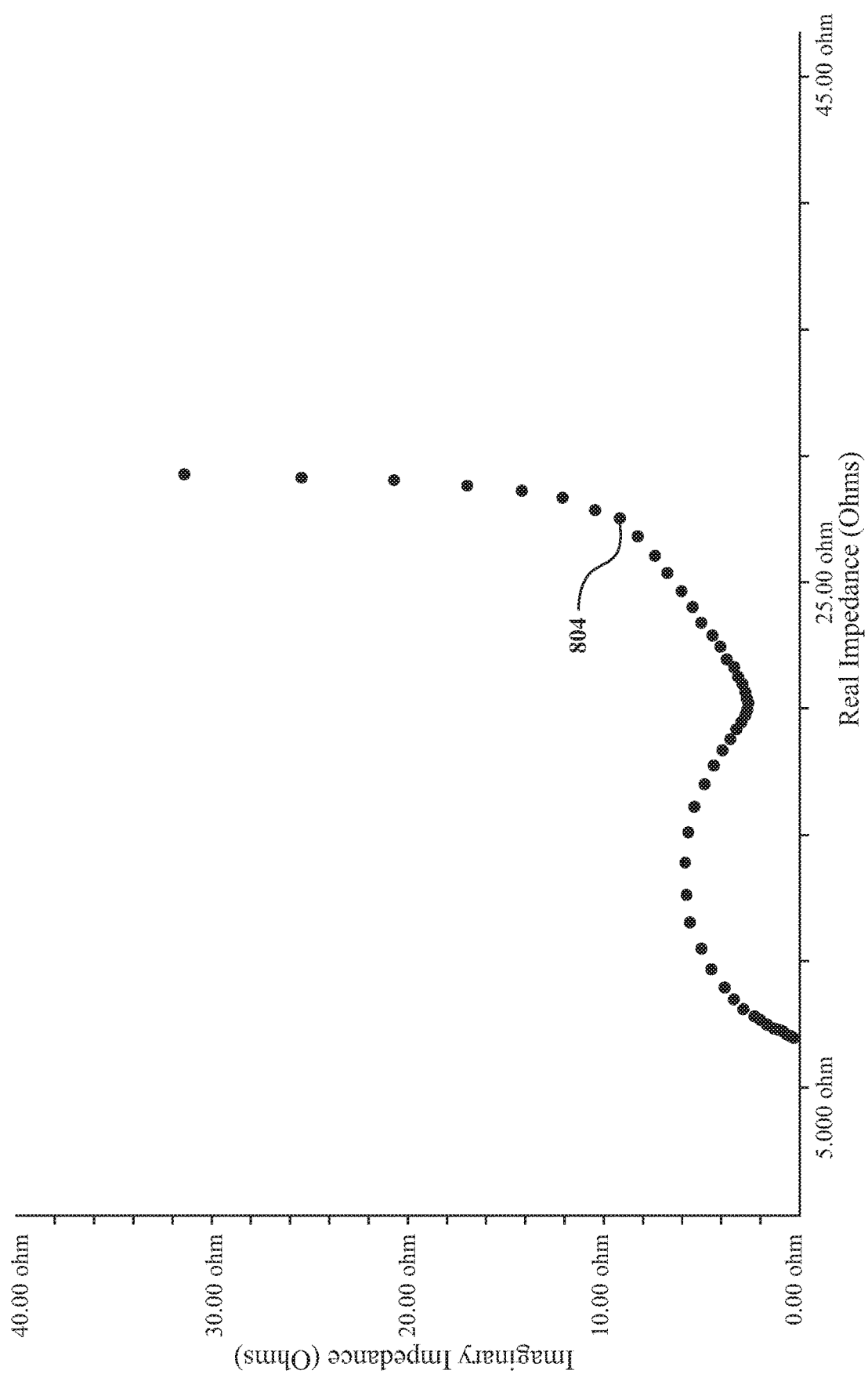
FIG. 8 depicts a Nyquist diagram showing an oxygen sensor response.
Figure 9:
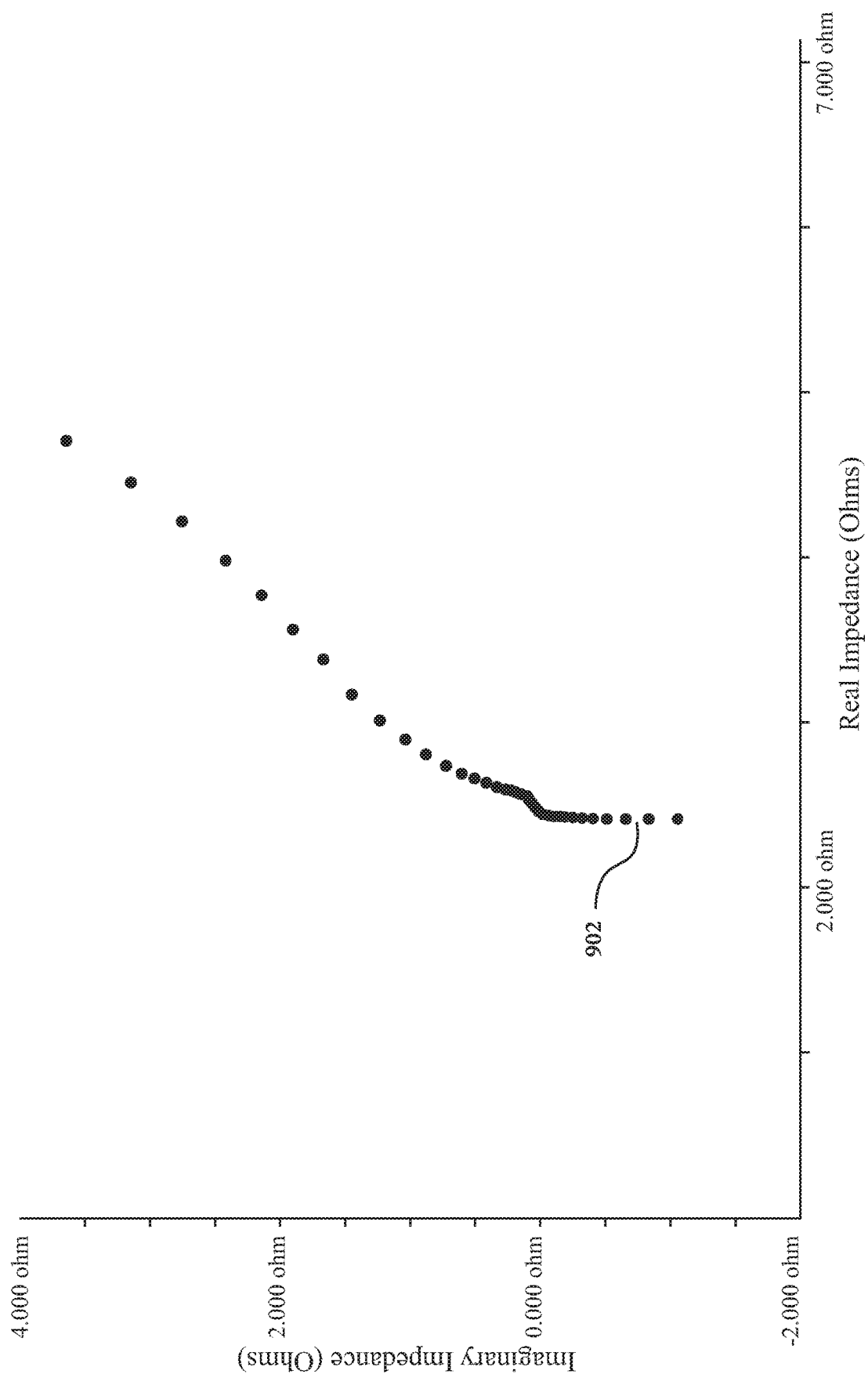
FIG. 9 depicts a Nyquist diagram showing a hydrogen sulfide sensor response.
Figure 10:
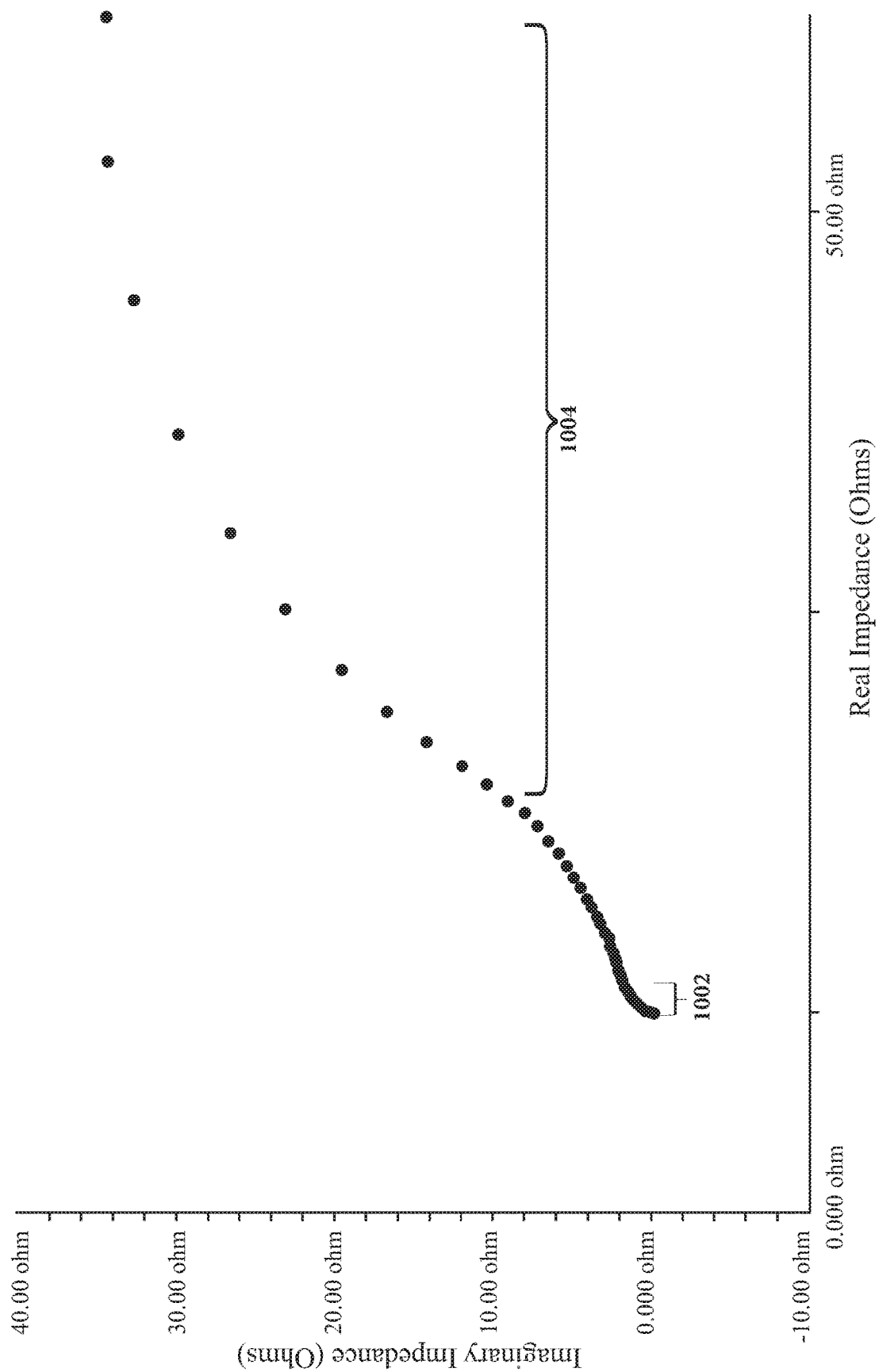
FIG. 10 depicts a Nyquist diagram showing an ammonia sensor response.

The system and methods of this disclosure may be used to evaluate the response of many different types of toxic gas electrochemical sensors 102. There may be differences in the response shape and levels for electrochemical sensors 102 sensitive to different types of toxic gases. FIGS. 8-10 show Nyquist plots illustrating changes in impedance measurements as an input waveform is varied in frequency from 0.1 Hz to 1 MHz for electrochemical sensors 102 sensitive to different types of toxic gases. While measurements of an oxygen (O2) electrochemical sensor 102 (FIG. 8) show a similar shape to the previous CO electrochemical sensors 102 measurements, the O2 electrochemical sensor has higher impedances and a more pronounced inflection point 804. Measurements of a hydrogen sulfide (H2S) electrochemical sensor 102, as shown in FIG. 9, don't have a circle portion similar to that of the CO electrochemical sensor 102 measurements. The set of points going straight down, labelled as 902, appear to be the result of stray inductance in the sensor and measurement system. As shown in FIG. 10, measurements of an ammonia (NH3) electrochemical sensor 102 describe two partial circles, a large partial circle 1002 on the right side of the graph and the start of a small partial circle 1004 on the left side of the graph.

In conclusion, a change in EIS spectrum of a gas sensor can yield a wealth of information about the sensor's internal operation. Furthermore, such changes in EIS spectrum may correspond with changes in the sensor's performance, such that the EIS spectrum can be used to predict sensor performance.

The methods and systems described herein may be deployed in part or in whole through a machine that executes computer software, program codes, and/or instructions on a processor. The processor may be part of a server, client, network infrastructure, mobile computing platform, stationary computing platform, or other computing platform. A processor may be any kind of computational or processing device capable of executing program instructions, codes, binary instructions and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer software on a server, client, firewall, gateway, hub, router, or other such computer and/or networking hardware. The software program may be associated with a server that may include a file server, print server, domain server, internet server, intranet server and other variants such as secondary server, host server, distributed server and the like. The server may include one or more of memories, processors, computer readable transitory and/or non-transitory media, storage media, ports (physical and virtual), communication devices, and interfaces capable of accessing other servers, clients, machines, and devices through a wired or a wireless medium, and the like. The methods, programs or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the disclosure. In addition, all the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client and the like. The client may include one or more of memories, processors, computer readable transitory and/or non-transitory media, storage media, ports (physical and virtual), communication devices, and interfaces capable of accessing other clients, servers, machines, and devices through a wired or a wireless medium, and the like. The methods, programs or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the disclosure. In addition, all the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements.

The methods, program codes, and instructions described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like.

The methods, programs codes, and instructions described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer to peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable transitory and/or non-transitory media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, stand-alone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or or intangible items from one state to another. The methods and systems described herein may also transform data representing physical and/or intangible items from one state to another.

The elements described and depicted herein, including in flow charts and block diagrams throughout the figures, imply logical boundaries between the elements. However, according to software or hardware engineering practices, the depicted elements and the functions thereof may be implemented on machines through computer executable transitory and/or non-transitory media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers and the like. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps thereof, may be realized in hardware, software or any combination of hardware and software suitable for a particular application. The hardware may include a dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the disclosure has been disclosed in connection with the preferred embodiments shown and described in detail, various modifications and improvements thereon will become readily apparent to those skilled in the art. Accordingly, the spirit and scope of the present disclosure is not to be limited by the foregoing examples, but is to be understood in the broadest sense allowable by law.

The use of the terms "a" and "an" and "the" and similar referents in the context of describing the disclosure (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The disclosure should therefore not be limited by the above described embodiment, method, and examples, but by all embodiments and methods within the scope and spirit of the disclosure.

All documents referenced herein are hereby incorporated by reference.

What is claimed is:

1. A system for evaluating a toxic gas electrochemical sensor, the system comprising:
    a potentiostat circuit electrically connected to the toxic gas electrochemical sensor;
    a voltage waveform generator connected to the potentiostat circuit and enabled to apply a voltage sine wave at a plurality of selected frequencies to a reference electrode of the toxic gas electrochemical sensor;
    a current measurement circuit electrically connected to the toxic gas electrochemical sensor for measuring an amplitude and a phase of a current through the toxic gas electrochemical sensor in response to the applied voltage sine wave; and
    a microcontroller electrically connected to the voltage waveform generator and the current measurement circuit, wherein the microcontroller controls the voltage waveform generator, receives a corresponding output from the current measurement circuit indicative of the amplitude and the phase of the current through the toxic gas electrochemical sensor at each of the plurality of selected frequencies, and analyzes the outputs from the current measurement circuit to determine information about a response time of the toxic gas electrochemical sensor, wherein analyzing the outputs comprises calculating a real impedance and an imaginary impedance corresponding to a current measurement at each of the plurality of selected frequencies resulting in calculated real impedances and calculated imaginary impedances and comparing a Nyquist plot of the calculated real impedances and the calculated imaginary impedances with a corresponding reference Nyquist plot of reference real impedances and reference imaginary impedances.

2. The system of claim 1, wherein an amplitude of the applied voltage sine wave is within a range of 5 mV to 50 mV.

3. The system of claim 1, wherein an amplitude of the applied voltage sine wave is within a range in which the toxic gas electrochemical sensor responds in a linear manner.

4. The system of claim 1, wherein the plurality of selected frequencies is within a frequency range of 0.1 Hz to 1 MHz.

5. The system of claim 4, wherein the plurality of selected frequencies includes at least some sequential frequencies that are spaced in unequal increments from each other.

6. The system of claim 1, wherein the reference real impedances and the reference imaginary impedances are obtained by measuring a newly calibrated toxic gas sensor over a frequency range.

7. The system of claim 1, wherein analyzing the outputs further comprises evaluating differences in a location of one or more features of the Nyquist plot of calculated impedances with a location of corresponding one or more features of the corresponding reference Nyquist plot of reference impedances, wherein the corresponding one or more features include at least one of a diameter of a semi-circle or a slope of a linear portion.

8. The system of claim 1, wherein if a change in the response time of the toxic gas electrochemical sensor is greater than a predetermined amount, then the microcontroller performs at least one of: updating a calibration for the toxic gas electrochemical sensor, updating a calibration for a piece of equipment associated with the toxic gas electrochemical sensor, disabling a piece of equipment associated with the toxic gas electrochemical sensor, or alerting a user.

9. The system of claim 1, wherein the toxic gas electrochemical sensor is one of a carbon monoxide sensor, an ammonia electrochemical sensor, a hydrogen sulfide sensor, and an oxygen sensor.

10. The system of claim 1, wherein the toxic gas electrochemical sensor is a three electrode sensor having the reference electrode, a working electrode, and a counter electrode.

11. The system of claim 10, wherein the current measurement circuit is connected to the working electrode or the counter electrode.

12. The system of claim 1, wherein the toxic gas electrochemical sensor includes either two or four electrode terminals.

13. The system of claim 1, wherein the toxic gas electrochemical sensor is a two electrode terminal sensor including a working electrode and the reference electrode, wherein the reference electrode is a combination counter/reference electrode.

14. The system of claim 1, wherein the toxic gas electrochemical sensor is a four electrode sensor able to detect at least two different detectable gases, wherein the four electrode sensor comprises the reference electrode, a counter electrode, and at least two working electrodes, wherein each of the at least two working electrodes corresponds to a respective one of the at least two different detectable gases.

15. The system of claim 14, wherein the current measurement circuit comprises at least two current measurement circuits, wherein each of the at least two current measurement circuits measures current at a respective one of the at least two working electrodes.

16. The system of claim 1, wherein the microcontroller analyzes the outputs from the current measurement circuit to determine information regarding a change in a bulk electrolyte resistance of the toxic gas electrochemical sensor, a change in a freedom of diffusion of ions within the toxic gas electrochemical sensor or a change in an effective polarization impedance of an electrode/electrolyte interface.

17. The system of claim 1, wherein information about the toxic gas electrochemical sensor comprises information regarding a change in the response time of the toxic gas electrochemical sensor.

18. The system of claim 1, wherein the microcontroller analyzes the outputs from the current measurement circuit to determine information about a rate of change of the response time of the toxic gas electrochemical sensor.

19. A method for evaluating a toxic gas sensor using electrochemical impedance spectroscopy, comprising:
    applying a current or a voltage sine wave at a plurality of selected frequencies to a reference electrode of the toxic gas sensor;

measuring a voltage or a current response of the toxic gas sensor corresponding to each of the plurality of selected frequencies; and analyzing the measured voltage response or the measured current response over the plurality of selected frequencies to determine information about a response time of the toxic gas sensor, wherein analyzing the measured voltage response or the measured current response comprises calculating a real impedance and an imaginary impedance corresponding to a current or a voltage measurement at each of the plurality of selected frequencies resulting in calculated real impedances and calculated imaginary impedances, and comparing a Nyquist plot of the calculated real impedances and the calculated imaginary impedances with a corresponding reference Nyquist plot of reference real impedances and reference imaginary impedances.

20. The method of claim 19, wherein information about the response time of the toxic gas electrochemical sensor comprises information regarding a change in the response time of the toxic gas electrochemical sensor.

21. The method of claim 19, wherein analyzing the measured voltage response or the measured current response further comprises evaluating differences in a location of one or more features of the Nyquist plot of calculated impedances with a location of corresponding one or more features of the corresponding reference Nyquist plot of reference impedances, wherein the corresponding one or more features include at least one of a diameter of a semi-circle or a slope of a linear portion.

22. A system for evaluating a toxic gas electrochemical sensor, comprising:
a galvanostat circuit electrically connected to the toxic gas electrochemical sensor;
a current waveform generator connected to the galvanostat circuit and enabled to apply a current sine wave at a plurality of selected frequencies to a reference electrode of the toxic gas electrochemical sensor;
a voltage measurement circuit electrically connected to the toxic gas electrochemical sensor for measuring an amplitude and a phase of a voltage across the toxic gas electrochemical sensor in response to the applied current sine wave; and
a microcontroller electrically connected to the current waveform generator and the voltage measurement circuit, wherein the microcontroller controls the current waveform generator, receives a corresponding output from the voltage measurement circuit indicative of the amplitude and phase of the voltage across the toxic gas electrochemical sensor at each of the plurality of selected frequencies, and analyzes the outputs to determine information about a response time of the toxic gas electrochemical sensor, wherein analyzing the outputs comprises calculating a real impedance and an imaginary impedance corresponding to a voltage measurement at each of the plurality of selected frequencies resulting in calculated real impedances and calculated imaginary impedances and comparing a Nyquist plot of the calculated real impedances and the calculated imaginary impedances with a corresponding reference Nyquist plot of reference real impedances and reference imaginary impedances.

23. The system of claim 22, wherein an amplitude of the applied current sine wave is within a range of 1 nA to 1 mA.

24. The system of claim 22, wherein the plurality of selected frequencies is within a frequency range of 0.1 Hz to 1 MHz.

25. The system of claim 22, wherein the microcontroller analyzes the outputs from the voltage measurement circuit to determine information regarding a change in a bulk electrolyte resistance of the toxic gas electrochemical sensor or a change in a freedom of diffusion of ions within the toxic gas electrochemical sensor.

26. The system of claim 22, wherein information about the response time of the toxic gas electrochemical sensor comprises information regarding a change in the response time of the toxic gas electrochemical sensor.

27. The system of claim 26, wherein if the change in the response time of the toxic gas electrochemical sensor is greater than a predetermined amount, then the microcontroller performs at least one of: updating a calibration for the toxic gas electrochemical sensor, updating a calibration for a piece of equipment associated with the toxic gas electrochemical sensor, disabling a piece of equipment associated with the toxic gas electrochemical sensor, or alerting a user.

28. The system of claim 22, wherein analyzing the outputs further comprises evaluating differences in a location of one or more features of the Nyquist plot of calculated impedances with a location of corresponding one or more features of the corresponding reference Nyquist plot of reference impedances, wherein the corresponding one or more features include at least one of a diameter of a semi-circle or a slope of a linear portion.

* * * * *